United States Patent
Guidi et al.

(10) Patent No.: US 11,813,360 B2
(45) Date of Patent: Nov. 14, 2023

(54) CARRIER PARTICLES FOR DRY POWDER FORMULATIONS FOR INHALATION

(71) Applicant: CHIESI FARMACEUTICI S.p.A., Parma (IT)

(72) Inventors: Tomaso Guidi, Parma (IT); Amrit Paudel, Parma (IT); Sarah Elizabeth Zellnitz, Parma (IT); Joana Filipa Fernandes Teixeira Pinto, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 171 days.

(21) Appl. No.: 17/262,802

(22) PCT Filed: Jul. 24, 2019

(86) PCT No.: PCT/EP2019/069943
§ 371 (c)(1),
(2) Date: Jan. 25, 2021

(87) PCT Pub. No.: WO2020/020957
PCT Pub. Date: Jan. 30, 2020

(65) Prior Publication Data
US 2021/0290540 A1    Sep. 23, 2021

(30) Foreign Application Priority Data
Jul. 27, 2018    (EP) .................... 18186078

(51) Int. Cl.
| | |
|---|---|
| *A61K 9/16* | (2006.01) |
| *A61K 9/00* | (2006.01) |
| *A61K 47/14* | (2017.01) |
| *A61P 11/00* | (2006.01) |

(52) U.S. Cl.
CPC .......... *A61K 9/1623* (2013.01); *A61K 9/0075* (2013.01); *A61K 9/1682* (2013.01)

(58) Field of Classification Search
CPC .. A61K 9/0075; A61K 9/1623; A61K 9/1682; A61K 47/14; A61P 11/00
See application file for complete search history.

(56) References Cited

U.S. PATENT DOCUMENTS

| | | | | |
|---|---|---|---|---|
| 2004/0043964 | A1* | 3/2004 | Gomi ........................ | C08L 1/02 424/494 |
| 2005/0043228 | A1* | 2/2005 | DeFelippis ............... | A61P 1/00 514/4.8 |
| 2008/0199527 | A1* | 8/2008 | Curatolo .............. | A61K 9/5026 424/494 |
| 2015/0352127 | A1* | 12/2015 | Brambilla ......... | A61M 15/0068 128/200.23 |

FOREIGN PATENT DOCUMENTS

| | | |
|---|---|---|
| EP | 2601973 A1 | 6/2013 |
| EP | 2273983 * | 7/2016 |
| WO | WO-0215880 A2 | 2/2002 |
| WO | WO-2011069197 A1 | 6/2011 |

OTHER PUBLICATIONS

Kanig, Properties of fused mannitol in compressed tablets; Journal of pharmaceutical science, vol. 53, No. 2, Feb. 1964. pp. 188-192. (Year: 1964).*
Extended European Search Report dated Jan. 29, 2019 in Application No. 18186078.4, 6 pages.
International Search Report and Written Opinion dated Oct. 15, 2019 in PCT/EP2019/069943, 10 pages.

* cited by examiner

*Primary Examiner* — Mina Haghighatian
(74) *Attorney, Agent, or Firm* — Element IP, PLC

(57) ABSTRACT

The present invention concerns carrier particles suitable for use in dry powder formulations for inhalation. The invention also relates to processes for their preparation by spray-congealing.

11 Claims, 5 Drawing Sheets

CARRIER PARTICLES FOR DRY POWDER FORMULATIONS FOR INHALATION

CROSS-REFERENCE TO RELATED APPLICATIONS

Figure 1:
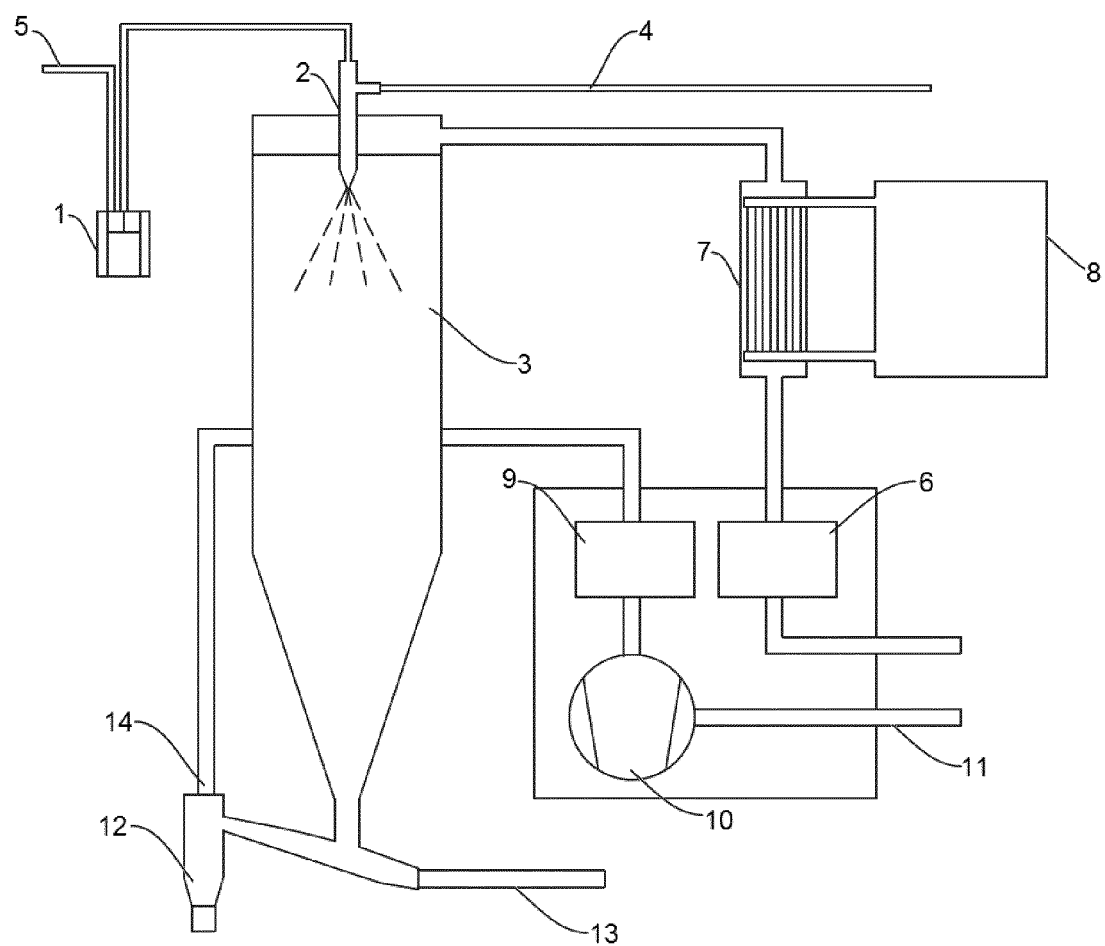

This application is the U.S. National Stage of International Application No. PCT/EP2019/069943, filed Jul. 24, 2019, and this application claims priority to European Patent Application No. EP 18186078.4, filed Jul. 27, 2018.

TECHNICAL FIELD

The present invention concerns carrier particles for use in dry powder formulations for inhalation and processes for preparation thereof.

BACKGROUND OF THE INVENTION

Dry powder inhalation (DPI) drug therapy has been used for many years to treat respiratory conditions such as asthma, chronic obstructive pulmonary disease (COPD), and systemic diseases.

Compared to oral drug intake, only relatively small doses are needed for effective therapy as first pass metabolism is by-passed and/or significantly reduced.

Such small doses reduce the body's exposure to the drug and minimize side effects. Systemic adverse effects are also reduced as topical lung delivery takes the drug directly to the site of action. Lower dosage regimens may also provide considerable cost savings, particularly where expensive therapeutic agents are concerned.

To be effectively delivered into the lungs, drug particles are required to have a particle size in the range of few micrometers, generally 1-5 microns.

Dry powder formulations are typically formulated by mixing the drug with coarse carrier particles, giving rise to ordered mixture where the micronized active particles adhere to the surface of the carrier particles whilst in the inhaler device.

The carrier makes the micronized powder less cohesive and improves its flowability, making easier handling the powder during the manufacturing process (pouring, filling, dosing, etc.). Furthermore, the carrier acts as bulk agent when the therapeutic dose of the drug is in the microgram range.

During inhalation, the drug particles separate from the surface of carrier particles, and penetrate the lower lungs, while the larger carrier particles are mostly deposited in the oropharyngeal cavity.

The detachment of drug particles from the carrier surface is regarded as the most critical factor which governs the availability of the medicament to the lungs. This will depend on the mechanical stability of the powder mix and on the way this is influenced by the adhesion characteristics between the drug and the carrier, and the external forces required to break up the non-covalent bonds formed between adhering particles. Too strong bonds between adhering particles may prevent the separation of the micronized drug particles from the surface of carrier particles.

Different approaches aimed at modulating the adhesion have been proposed in the art to promote the release of the drug particles from the carrier particles and, hence, to increase the respirable fraction. For instance, to satisfy said purpose, the addition of fine excipient particles and/or fine additives with lubricant or anti-adherent properties (hereinafter collectively fine particles) has been suggested as a solution of the technical problem. Typically, said fine particles have a size of less than 50 microns, preferably of less than 20 microns.

However, since fine particles have poor flow properties, the flowability properties of the relevant powder formulations tend to get worse as the fine particle content increases.

On the other hand, the inhalation route is more and more utilized for active ingredients to be administered at rather high single doses.

This is becoming a challenging task as it is well known that higher the dose, and hence concentration of the active ingredient, the higher is the risk of forming uneven agglomerates (i.e. micronized drug particles held together by strong cohesive forces) which are detrimental to the possibility of achieving a good uniformity of distribution of the drug in the powder mixture and hence a good accuracy of the dose as well as to the suitable de-aggregation upon inhalation by the patient. Moreover, the higher the dose and hence concentration of the active ingredient, the higher may be the number of fine particles required for having a satisfying respirable fraction.

A high amount of a micronized active ingredient and/or and fine excipient particles may have a detrimental effect on the flowability of the relevant formulation, which in turn would impact on the device capability of delivering the correct dose upon activation of the inhaler.

Therefore, it would be advantageous to provide carrier particles capable of accommodating rather high amounts of micronized drugs, without jeopardizing the flow properties of the relevant powder formulations.

It would even be more advantageous to provide carrier particles capable of accommodating rather high amounts of micronized drugs, while maintaining good aerosol performances without the use of fine excipient particles and/or fine additives.

The problem is solved by the carrier particles of the present invention and processes of preparation thereof.

SUMMARY OF THE INVENTION

In a first aspect, the present invention is directed to melt-spray solidified particles (e.g. spray congealed) made of mannitol to be used as a carrier for dry powder formulations for inhalation, said particles having a mass diameter in the range of from 10 to 300 micrometers, whereby said particles are characterized by a regular shape represented by a shape factor comprised between 0.80 and 1.00, preferably between 0.90 and 1.00, more preferably between 0.95 and 1.00.

In a second aspect, the invention is directed to the above carrier particles obtainable by a process comprising the steps of:
  i) heating mannitol until complete melting;
  ii) spraying the molten mannitol by a suitable nozzle into the spray congealing chamber to obtain droplets;
  iii) cooling the droplets to induce solidification and particle formation;
  iv) separating the obtained particles; and
  v) subjecting the particles to a conditioning step.

In a third aspect, the invention is directed to the above carrier particles obtained by a process comprising the steps of:
  i) heating mannitol until complete melting;
  ii) spraying the molten mannitol by a suitable nozzle into the spray congealing chamber to obtain droplets;
  iii) cooling the droplets to induce solidification and particle formation;

iv) separating the obtained particles; and v) subjecting the particles to a conditioning step.

In a fourth aspect, the invention is directed to a process for preparing the claimed spray-congealed particles, said process comprising the following steps:

i) heating mannitol until complete melting;

ii) spraying the molten mannitol by a suitable nozzle into the spray congealing chamber to obtain droplets;

iii) cooling the droplets to induce solidification and particle formation;

iv) separating the obtained particles; and v) subjecting the particles to a conditioning step.

In a fifth aspect, the invention concerns a pharmaceutical composition in form of dry powder for inhalation comprising the carrier particles of the invention and one or more active ingredients.

In a sixth aspect, the invention concerns a dry powder inhaler filled with the aforementioned dry powder pharmaceutical composition.

In a seventh aspect, the invention concerns a process for preparing the aforementioned pharmaceutical composition comprising a step of mixing the carrier particles of the invention with one or more active ingredients in a high-shear mixer.

In a further aspect, the invention is also directed to a package comprising a dry powder pharmaceutical formulation according to the invention and a dry powder inhaler.

Definitions

Unless otherwise specified, the terms 'active drug', 'active ingredient', 'active' and 'active substance', 'active compound' and 'therapeutic agent' are used synonymously.

The term 'microns' is used synonymously with 'micrometers'.

In general terms, the size of the particles is quantified by measuring a characteristic equivalent sphere diameter, known as volume diameter, by laser diffraction.

The particle size can also be quantified by measuring the mass diameter by means of suitable instruments and techniques known to the skilled person, such as sieving.

The volume diameter (VD) is related to the mass diameter (MD) by the density of the particles (assuming the size is independent from the density of the particles).

Alternatively, the particle size may be expressed in terms of volume diameter. In particular, the particle size distribution may be expressed in terms of: i) the volume median diameter (VMD) which corresponds to the diameter of 50 percent by weight of the particles, e.g d(v0.5), and ii) the volume diameter (VD) in micron of 10% and 90% of the particles, respectively, e.g d(v0.1) and d(v0.9).

The term 'fine particles' refers to particles having a volume median diameter preferably lower than 20 microns, more preferably lower than 15 microns, made of a physiologically acceptable excipient and/or made of an additive with lubricant or anti-adherent properties, or mixture thereof.

The term 'good flow properties' refers to a formulation that is easily handled during the manufacturing process and is capable of ensuring an accurate and reproducible delivery of the therapeutically effective dose.

Flow characteristics can be evaluated by measuring the Carr's index; a Can's index of less than 25 is usually taken to indicate good flow characteristics.

Alternatively flow characteristics can be evaluated by measuring the flow function coefficient (ffc) with a shear cell module of a powder rheometer. By the ffc value the powder can be classified as hardened (ffc≤1), greatly cohesive (ffc 1-2), cohesive (ffc 2-4) to easily flowing (ffc 4-10), and free flowing (ffc≥10). A value of above 10 is usually taken to indicate a free flowing powder and good flow characteristics.

The expression 'good homogeneity' refers to a formulation wherein, upon mixing, the content uniformity of the active ingredient, expressed as relative standard deviation (RSD), is less than 5%.

The expression 'physically stable in the device before use' refers to a formulation wherein the active particles do not substantially segregate and/or detach from the surface of the carrier particles both during manufacturing of the dry powder and in the delivery device before use.

The expression 'respirable fraction' refers to an index of the percentage of active ingredient particles which would reach the deep lungs in a patient. The respirable fraction, also termed fine particle fraction (FPF), is commonly evaluated using a suitable in vitro apparatus, typically the Multistage Cascade Impactor or Multi Stage Liquid Impinger (MLSI), Fast Screening Impactor (FSI) or Next Generation Impactor (NGI) according to procedures reported in common Pharmacopoeias. It is calculated by the ratio between the respirable dose and the delivered (emitted) dose.

The delivered dose is calculated from the cumulative deposition of the drug in the apparatus stages, while the respirable dose (fine particle dose) is calculated from the deposition in the stages corresponding to particles having a diameter ≤5.0 microns. The skilled person in the art shall adjust other parameters such as the inspiration flow, according to the guidelines reported in common Pharmacopeias.

A respirable fraction higher than 30% is an index of good inhalatory performance.

The term 'therapeutically effective amount' means the amount of active ingredient that when delivered to the lungs via a dry powder formulation as described herein provides the desired biological effect.

Figure 5:
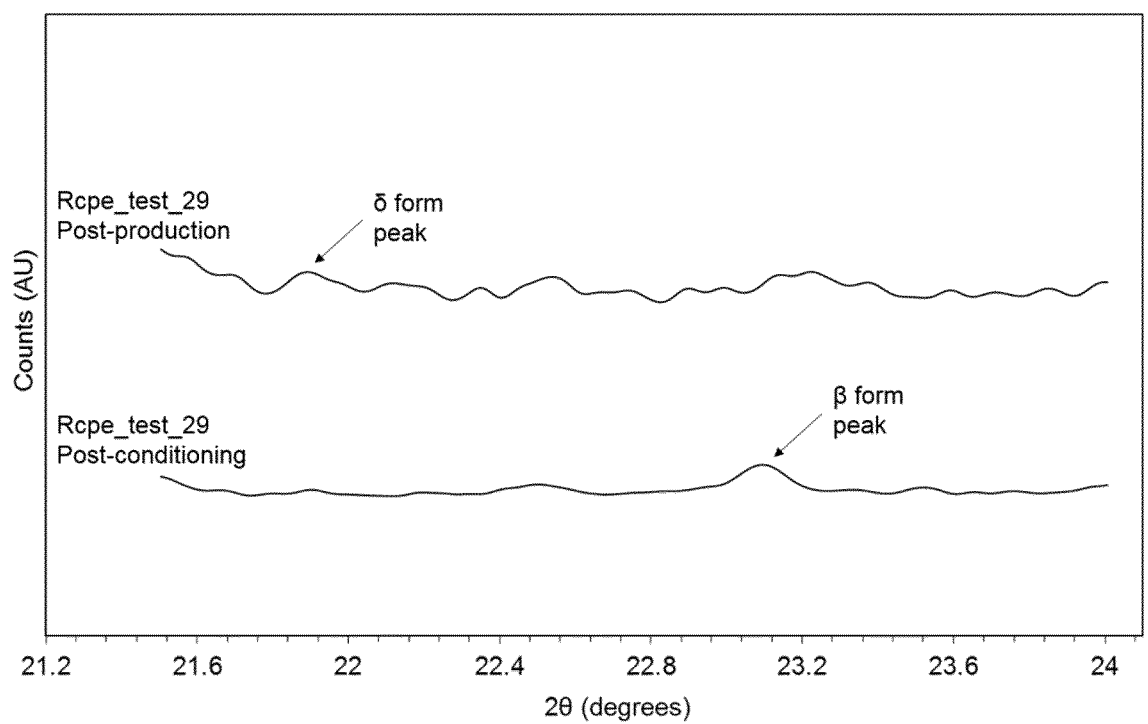

'Single dose' means the quantity of active ingredient administered at one time by inhalation upon actuation of the inhaler.

'Actuation' means the release of active ingredient from the device by a single activation (e.g. mechanical or breath).

The term 'rather high single therapeutically effective dose' means a nominal dose equal to or higher than 800 micrograms (μg).

The term 'high-shear mixer' refers to a mixer wherein a rotor or impeller, together with a stationary component known as a stator, is used in a tank containing the powder to be mixed to create a shear.

The term 'mannitol' refers to the three polymorphic forms of mannitol: α, β and δ. The β form is the thermodynamic stable form at 20° C. and greater. The δ form is the lowest melting form of mannitol. The δ form is thermodynamically unstable and can spontaneously transform to the more thermodynamically stable form β. Polymorphic transition from δ-to-β can be triggered by, for example, moisture.

FIGURES

FIG. 1—A schematic diagram of a spray-congealing apparatus.

FIG. 2—SEM pictures of mannitol particles.

FIG. 3—WAXS pattern of spray congealed mannitol over 6 months (stability study).

FIG. 4—WAXS pattern of spray congealed mannitol post preparation and post conditioning.

FIG. 5—WAXS pattern of spray congealed mannitol post preparation and post conditioning (zoomed in).

Figure 6:
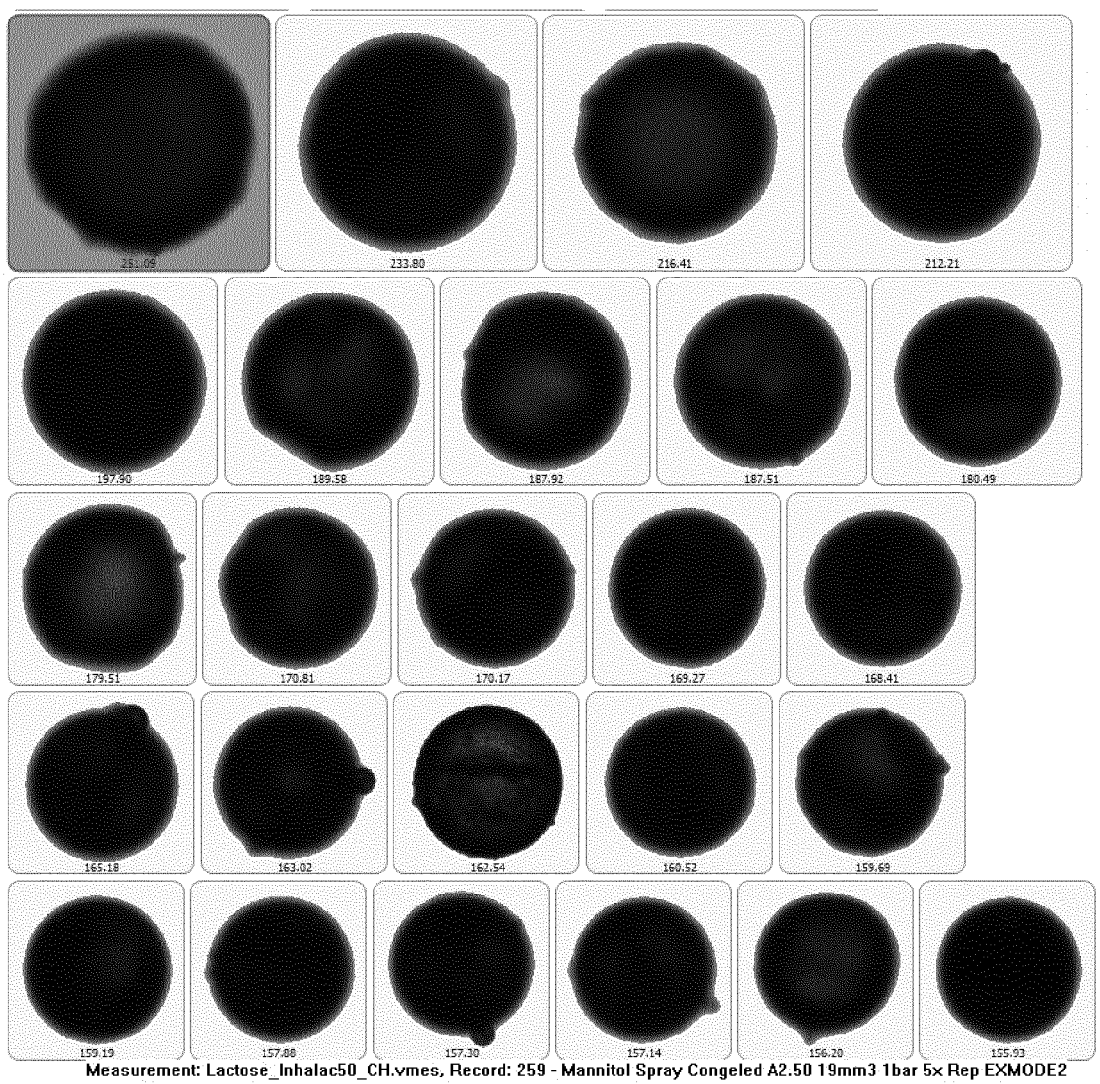

FIG. 6—Optical Microscopy Pictures.

DETAILED DESCRIPTION OF THE INVENTION

The invention is directed to spray-congealed particles made of mannitol to be used as a carrier for dry powder formulations for inhalation.

Spray congealing, also known as spray cooling, is a solvent-free process that transforms a melt into well-defined spherical particles.

A representative schematic diagram of a spray-congealing apparatus is reported in FIG. 1:

The molten sample is fed from a heated liquid container (1) to a heated nozzle (2) spraying the sample into a congealing chamber (3). The heated nozzle and the heated container are connected to compressed gas supply lines (4) and (5). Air is fed to the top of the congealing chamber (3) via an inlet HEPA (High Efficiency Particulate Air) filter (6) connected to a heat exchanger (7) and chiller unit (8). Air from the chamber (3) is discharged via an outlet HEPA filter (9) and a fan (10) to an exhaust outlet (11).

The dry particles are recovered from the bottom of the congealing chamber (3) via an outlet conduit (12) fed with compressed gas supplied from gas supply lines (13) and (14).

Other similar apparatus could be used working on the same principles.

Mannitol is utilized in view of the fact that, contrary to other sugars such as lactose, no degradation occurs during melting.

All the particles shall have a particle size, expressed as mass or volume diameter, in the range of 10 to 300 micrometers, preferably 20 to 280 micrometers, more preferably 30 to 250 micrometers.

In a preferred embodiment of the invention, when expressed as volume diameter, the particle size distribution of the carrier particles fulfills the following parameters: d(v,0.1) comprised between 25 and 45 microns, d(v,0.5) comprised between 70 and 110 microns and d(v,0.9) comprised between 150 and 220 microns.

The width of the particle size distribution of said carrier particles, expressed as a span, could advantageously be comprised between 1.3 and 2.2, preferably between 1.6 and 2.0. According to Chew et al J Pharm Pharmaceut Sci 2002, 5, 162-168, the span corresponds to [d(v,0.9)–d(v,0.1)]/d(v,0.5).

The shape factor is used to characterize the shape of the carrier particles of the invention.

Accordingly, the carrier particles of the invention are characterized by a shape factor comprised between 0.80 and 1.00, preferably between 0.90 and 1.00, more preferably between 0.95 and 1.00.

The shape factor can be determined according to the following equation reported in Kumar S et al Curr Appl. Phys. *Influence of metal powder shape on drag coefficient in a spray jet,* 2009, 9, 678-682

$$SF = 1/RN$$

wherein:

RN indicates the roundness of the particle and is calculated by applying the following formula:

$$RN = p^2/4\pi A$$

wherein p and A are the mean perimeter and area values, respectively, of ten spherical particles as measured from scanning electron microscopy (SEM) images.

Alternatively, the mean perimeter and area may be measured by an optical microscope.

In Kumar S et al it is reported that the shape factor (SF) of a circle is 1.00. It is also reported that deviation from unity leads to irregularity of the particle, but particles with a SF value higher than 0.8 can be considered having a spherical shape.

In a typical embodiment, the generated carrier particles showed a shape factor of 0.986 measured by Malvern Morphology G3 Ver. 8.12 (Malvern Instruments Inc, Pennsylvania, USA).

Scanning electron microscopy (SEM) or optical microscopy may also be used to qualitatively appreciate the characteristics of the powder microparticles of the invention such as particles' shape and their surface morphology.

The carrier particles of the invention show improved flowability that could, for instance, be measured with an FT4 powder rheometer (Freeman Technology, Tewkesbury, United Kingdom). Accordingly, the carrier particles of the invention are characterized by a ffc value above 10, typically between 14 and 16.

Several other methods may also be used to determine the characteristics of the carrier particles of the invention, for example true density, apparent and tapped densities, and the Specific Surface Area.

The true density of the particles of the invention may be measured by helium pycnometry (pycnometer: AccuPyc II 1340, Micromeritics, Norcross, Ga., USA) according to the following procedure: 20 purges at 19.5 psi and five analytical runs at 19.5 psi with an equilibration rate of 0.0050 psi/min. Particle volume is measured, allowing the calculation of particle density.

Typically, the true density is comprised between 1.3 and 1.6 g/cm$^3$, preferably between 1.4 and 1.5 g/cm$^3$.

The apparent and tapped densities can be determined according to known methods.

For instance, a sample is inserted in a 10 mL cylinder to reach 70-90% of the volume (the exact weight and height in the cylinder is recorded).

The apparent bulk density (ABD) is determined by the formula $$ABD = M/V0 \text{ (expressed in g/mL)}$$

where M is the weight of the sample and V0 is the initial volume of the sample in the cylinder.

Typically, the apparent bulk density is comprised between 0.55 and 0.75 g/ml, preferably between 0.6 and 0.7 g/ml.

Progressive number of taps are applied: 10, 40, 50, 100, 300, 250 and 500 and corresponding tapped bulk volume are registered. The analysis is completed at 1250 taps in total if the height does not change from 250 to the 500 taps step: if a change is observed, additional 1250 taps are added till the equilibrium is reached.

The tapped bulk density (TBD) is measured using the following formula:

$$TBD = M/Vt \text{ (expressed in g/mL)}$$

where M is the weight of the sample and Vt is the final volume of the sample in the cylinder.

Typically, the tapped bulk density is comprised between 0.7 and 0.9 g/ml, preferably between 0.75 and 0.85 g/ml.

From the ABD and the TBD, the Can's index can be calculated using the following formula:

$$\text{Carr's Index} = 100 \times (TBD - ABD)/TBD \text{ (expressed in \%)}$$

Typically, values turned out to be much lower than 25, indicating that the carrier particles of the invention are endowed with good flow characteristics.

The Specific Surface Area can be determined by Brunauer-Emmett-Teller (BET) nitrogen adsorption method according to a known procedure.

The Specific Surface Area of the carrier particles of the invention is comprised between 0.09 and 0.26 m$^2$/g, preferably between 0.10 and 0.20 m$^2$/g.

Surprisingly, the pharmaceutical formulations comprising the carrier particles of the invention can give rise to good aerosol performances without the use of fine excipient particles and/or fine additives.

Furthermore, if the blending occurs in a high shear mixer for short mixing times (equal or less than 20 minutes), said formulations exhibit a good homogeneity of active ingredients to be delivered at rather high doses, for example at 800 micrograms per shot of the inhaler.

However, good homogeneity can be achieved by subjecting the powder to longer mixing times using conventional mixers.

Said optimal characteristics are the results of the process utilized for preparing the carrier particles.

Therefore, the invention is directed to a process for preparing the carrier particles of the invention, said process comprising the following steps:

i) heating mannitol until complete melting;

ii) spraying the molten mannitol by a suitable nozzle (2) into the spray congealing chamber (3) to obtain droplets;

iii) cooling the droplets to induce solidification and particle formation;

iv) separating the obtained particles; and v) subjecting the particles to a conditioning step.

Mannitol is commercially available, and can be used in each of its crystalline polymorphic forms (α, β and δ form) and/or a mixture of them as well as amorphous and/or crystalline form as well as a mixture of them.

Spray-congealing apparatus are commercially available for example from ProCepT (Zelzate, Belgium).

Advantageously, in step i), mannitol is heated to a temperature of least 185° C., preferably of 190 to 200° C. under vacuum.

In step ii), as a suitable nozzle a bi-fluid nozzle could be used.

Alternatively other types of nozzles such as ultrasonic atomizer and rotary atomizer could be advantageously utilized.

The parameters related to the type of nozzle, its inner diameter, the pressure, and the spraying rate shall be adjusted by the skilled person depending on the size of the batch.

Typically, for obtaining carrier particles with the particle size as claimed, the inner diameter of a bi-fluid nozzle is 1.2 mm and the spraying rate is adjusted to a range between 18.3 and 21.5 g/min. Nozzle air is adjusted to 5 l/min corresponding to a pressure of 0.44 bar.

The cooling of the droplets in step iii) can be achieved at ambient temperature or by applying cooling air during spraying at a temperature of at least −10 to −20° C.

In some apparatus, spray-melt solidification of the particles can be achieved by pouring the droplets into liquid nitrogen.

In step iv), the particles are then separated from the gas stream in, for example, a cyclone and/or a filter bag.

Since, during solidification, formation of the metastable δ form of mannitol occurs, the particles in step v) are subjected to a conditioning step to convert the metastable form into the stable β form.

Advantageously, the conditioning step is performed by exposing the powder at room temperature in a sealed chamber to a 90-97% relative humidity, preferably 93%, for 12-48 hours, preferably 24 hours.

The desired humidity environment could be obtained with a saturated salt solution of potassium sulfate or potassium nitrate, preferably potassium nitrate.

Transition from δ-form to β-form can be monitored by DSC and or WAXS analysis according to procedures known to the skilled person.

Once all the δ-form is converted into the more stable polymorphs no further changes can be observed.

Wide angle x-ray (WAXS) scattering can be used to determine the crystallinity and polymorphic forms of the powder samples. Measurements should be carried out at room temperature using a point-focusing camera system S3-MICRO camera (Bruker AXS GmbH, Germany). The samples should be filled into 2 mm diameter glass capillaries and analyzed under constant rotation (9 rpm/min) during 600 s at 30 counts/s.

WAXS results post-conditioning can reveal the disappearance of the 6 form characteristic Bragg peak at ca. 22° and the appearance of β form most preeminent Bragg peak at ca. 23°. If this is the case, it can be concluded that the selected conditioning procedure was successful in producing the wished δ-to-β polymorphic transition.

Alternatively, a differential scanning calorimeter (DSC 204F1 Phoenix®, Netzsch GmbH, Selb, Germany) with the following settings could be used for solid-state characterization.

Samples mass of 10-12 mg (n=3)

sealed aluminum pans with the pierced lid heating from 25 to 200° C. at a heating rate of 10° C./min using pure nitrogen as purging gas at a flow rate of 20 mL/min.

Mannitol particles are substantially present in a crystalline form.

Advantageously the extent of crystallinity, expressed as weight % of the crystalline particles with respect to the total weight of the particles, is higher than 90%, preferably higher than 95%.

The crystallinity and extent thereof may be determined using X-ray powder diffraction or other techniques known to the skilled person such as differential scanning calorimetry (DSC), wide angle x-ray scattering (WAXS) or microcalorimetry.

The conditioned carrier particles turned out to be physically stable for at least 6 months at room temperature, making possible to provide stable pharmaceutical formulations.

Therefore, the invention is also directed to a pharmaceutical composition in form of dry powder for inhalation comprising the carrier particles of the invention in a physical admixture with one or more active ingredients.

The active ingredient may be practically any pharmaceutically active compound which can be administered by inhalation in dry powders.

In order that the active substance is inhalable, i.e. it can pass into the deep lung such as the terminal and respiratory bronchioles and the alveolar ducts and sacs, it must be in particulate form having a mean particle diameter (measured as the mass mean diameter) of at most about 10 microns, e. g. from 1 to 10 microns, and preferably 1 to 6 microns. Such micronized particles may be obtained in a manner known per se, for example by micronization, controlled precipitation from selected solvents, spray drying, supercritical fluids, or according to the processes described in WO 2004/073827, WO 2008/155570, WO 2008/114052 and WO 2010/007447.

The therapeutically effective amount of the active substance may vary within wide limits depending on the nature of the active substance, the type and severity of the condition to be treated and the condition of the patient in need of treatment.

Typically, the active substance particles are added to the carrier particles of the invention by mixing according to known procedures, preferably in a high-shear mixer.

Typical high-shear mixers are P 100 and P 300 (Diosna GmbH, Germany), Roto Mix (IMA, Italy), and Cyclomix™ (Hosokawa Micron Group Ltd, Japan).

In particular, the rotation speed of the mixer and the time of mixing shall be adjusted by the skilled person to obtain a good uniformity of distribution of the active ingredient in the formulation.

Typically, an excellent uniformity of distribution of the active ingredient is achieved in a high-shear mixer upon applying a mixing time of at least 5 minutes and a speed of 100-500 r.p.m, preferably for 20 minutes at a speed of 100-250 r.p.m.

As an example, the active ingredients may be chosen from short-acting and long-acting beta$_2$-agonists such as terbutalin, reproterol, salbutamol, salmeterol, formoterol, carmoterol, milveterol, indacaterol, olodaterol, fenoterol, clenbuterol, bambuterol, broxaterol, epinephrine, isoprenaline or hexoprenaline or salts and/or solvate forms thereof; short-acting and long-acting anticholinergics such as tiotropium, ipratropium, oxitropium, oxybutynin, aclidinium, trospium, glycopyrronium, or the compounds known with the codes GSK 573719 and GSK 1160274, or salts and/or solvate forms thereof; bifunctional Muscarinic Antagonist-beta2 Agonist (MABA) compounds for inhalation such as GSK 961081; neutrophil elastase inhibitors such as ONO-6818 and MK0339; p38 map kinase inhibitors such as VX-702, SB-681323 and GW-856553; short-acting and long acting corticosteroids such as butixocart, rofleponide, flunisolide budesonide, ciclesonide, mometasone and its ester, i.e. furoate, fluticasone and its ester, i.e. propionate and furoate, beclomethasone and its ester, i.e. propionate, loteprednol or triamcinolone acetonide and solvate forms thereof; leukotriene-antagonists, such as andolast, iralukast, pranlukast, imitrodast, seratrodast, zileuton, zafirlukast or montelukast; phosphodiesterase-inhibitors, such as filaminast, piclamilast or roflumilast; an PAF-Inhibitor, such as apafant, rorapafant or israpafant; pain killers such as morphine, fentanyl, pentazocine, buprenorphine, pethidine, tilidine, or methadone; potency agents such as sildenafil, alprostadil or phentolamine; or a pharmaceutically acceptable derivative or salt of any of the foregoing compounds or classes of compounds. In as much as any of these compounds possess chiral centers, the compounds can be used in optically pure form, or can be presented as diastereomeric mixtures or racemic mixtures.

Dry powder formulations may also contain as active ingredients, antibiotics such as ciprofloxacin, levofloxacin, colistin, tobramycin, amikacin and gentamicin; proteins such as insulin and al-antitrypsin; antiviral drugs such as zanamivir and ribavirin; antifungal agents such as itraconazole, and phosphodiesterase (PDE)-5 inhibitors such as sildenafil and tadalafil. Preferably, the dry powder formulations for inhalation comprising the carrier particles of the invention and one or more active ingredients selected from the classes of bifunctional Muscarinic Antagonist-beta$_2$ Agonist (MABA) compounds, neutrophil elastase inhibitors, p38 map kinase inhibitors, short-acting and long acting corticosteroids, and phosphodiesterase-inhibitors.

The concentration of the active ingredient in the powder formulation will depend on the shot weight of the formulation delivered upon actuation of the inhaler.

For example, considering an expected single dose of 800 micrograms, if the shot weight of the formulation delivered upon actuation of the inhaler is 10 mg, this would correspond to a concentration of the active ingredient of 8% w/w.

Analogously, for a shot weight of 20 mg, the concentration of the active ingredient would be of 4% w/v.

In a preferred embodiment, the dry powder formulations comprising the carrier particles of the invention are particularly useful for the administration of active ingredients to be delivered at single doses per actuation of the inhaler ranging from 800 micrograms to 1 mg.

Although it is not essential to achieve good aerosol performances, the powder formulation may further comprise a fraction of fine particles having a median volume diameter lower than 20 microns, more advantageously lower than 15 microns, preferably lower than 10 microns.

Said fine particles may be made of a physiologically acceptable excipient as defined above and/or may be made of an additive material selected from the class of the anti-adherents such as the amino acids, for example leucine and isoleucine, or from the class of lubricants such as magnesium stearate; sodium stearyl fumarate, stearyl alcohol, stearic acid, and sucrose monopalmitate.

In a particular embodiment, the fine particles may be composed of particles of a physiologically acceptable excipient and particles of an additive in any ratio, and they are prepared according to the teaching of WO 01/78695.

In another embodiment, the fine particles may consist of a mixture of 90 to 99.5 percent by weight of particles of alpha-lactose monohydrate and 0.5 to 10 percent by weight of magnesium stearate, wherein at least 90% of said particles have a volume diameter lower than 12 microns, and the volume median diameter of said particles is comprised between 4 and 6 microns.

Said fine particles could be added to the formulation and mixed according to known methods.

The dry powder formulation for inhalation comprising the carrier particles of the invention may be utilized with any dry powder inhaler.

Dry powder inhalers can mainly be divided in: i) single-dose (unit-dose) inhalers, for the administration of single subdivided doses of the active compound; ii) pre-metered multi-dose inhalers or reservoir inhalers pre-loaded with quantities of active principles sufficient for longer treatment cycles.

The dry powder formulations may be presented in unit dosage form. Dry powder compositions for topical delivery to the lung by inhalation may, for example, be presented in capsules and cartridges of for example gelatin, or blisters of for example laminated aluminum foil, for use in an inhaler or an insufflator.

The dry powder formulation for inhalation according to the invention is particularly suitable for multi-dose dry powder inhalers comprising a reservoir from which individual therapeutic dosages can be withdrawn on demand through actuation of the device.

A preferred multi-dose device is the inhaler described in WO 2004/012801, in particular from page 1, first line to page 39, last line.

Other multi-dose devices that may be used are for instance the ELLIPTA™ or DISKUS™ of GlaxoSmithKline, the TURBOHALER™ of AstraZeneca, TWISTHALER™ of Schering and CLICKHALER™ of Innovata.

As marketed examples of single-dose devices, there may be mentioned ROTOHALER™ of GlaxoSmithKline and HANDIHALER™ of Boehringer Ingelheim.

The following examples illustrate in detail the invention.

Example 1—Preparation of Mannitol Carrier Particles of the Invention

Mannitol Pearlitol 300DC was purchased from Roquette (France).

A spray congealing apparatus available from ProCepT (Belgium) was used.

Three different samples were prepared (60 g, 2×500 g comprising of 4 times 125 g).

Mannitol was heated at 200° C. under vacuum until complete melting and sprayed through a bi-fluid nozzle of 1.2 mm inner diameter, applying cooling air in the chamber of a temperature of −7° C. to −10° C. (temperature set point chiller−20° C.), into the solidification chamber.

The obtained particles (yield: about 45%) were separated from the gas stream in a cyclone.

Figure 3:
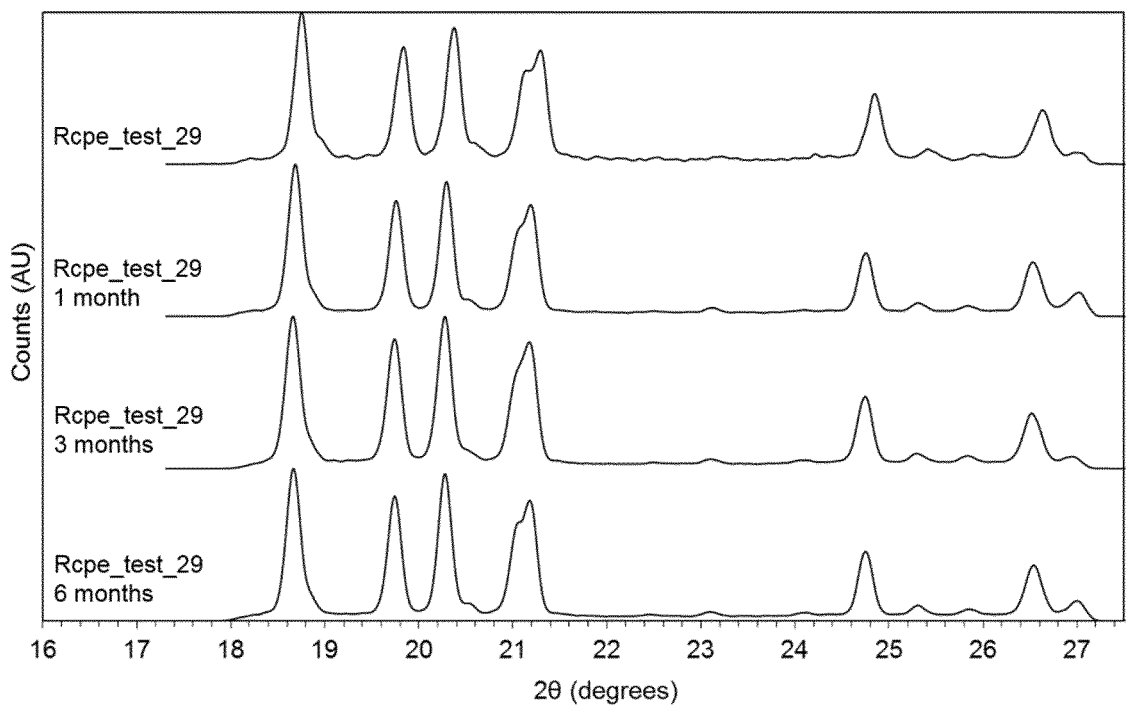
Figure 4:
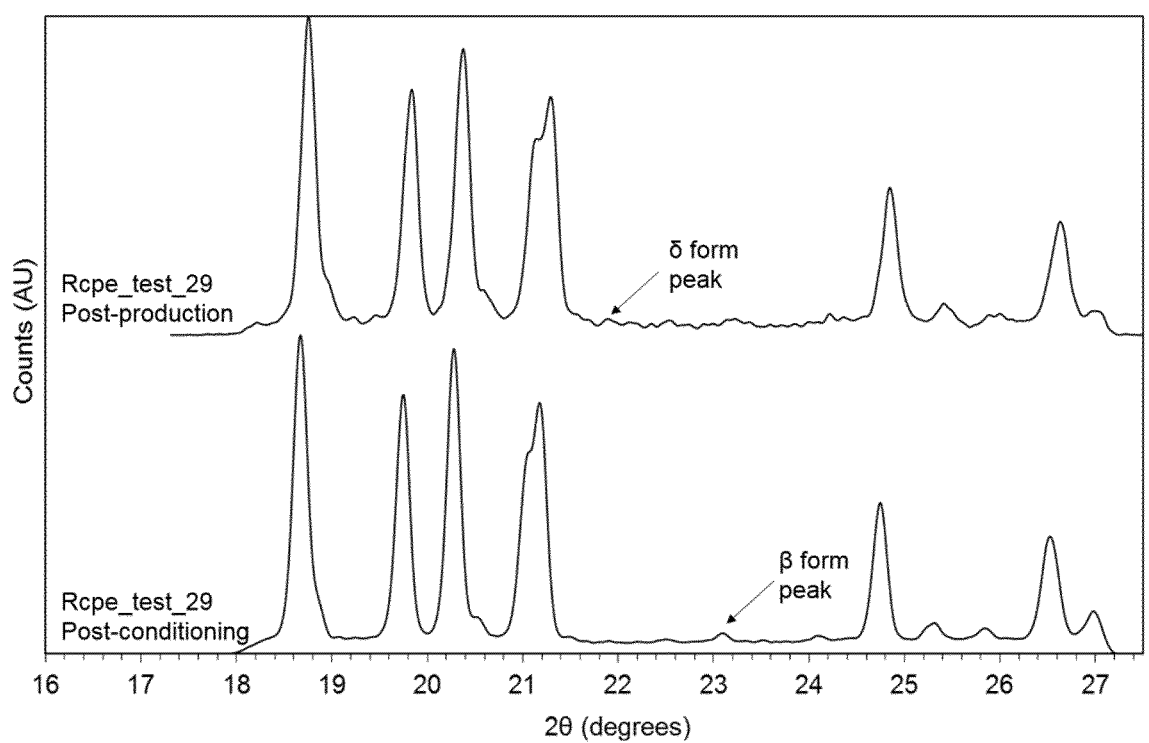

Formation of δ mannitol during spray-congealing raised a concern about the stability of the final particles. In fact, δ form is a metastable polymorph of mannitol which has 2 stable polymorphs (α and β). One-month stability study of the selected Spray Congealed batch showed that the δ form detected after WAXS is converting into the stable β or α form over time (FIG. 3). However, the δ form could be successfully converted into a stable β mannitol with a conditioning step post-Spray Congealing (24 h at 93% RH set with saturated salt solution of potassium nitrate in a sealed chamber) (FIGS. 4 and 5). The conditioned material is stable up to 6 months (FIG. 3).

Figure 2:
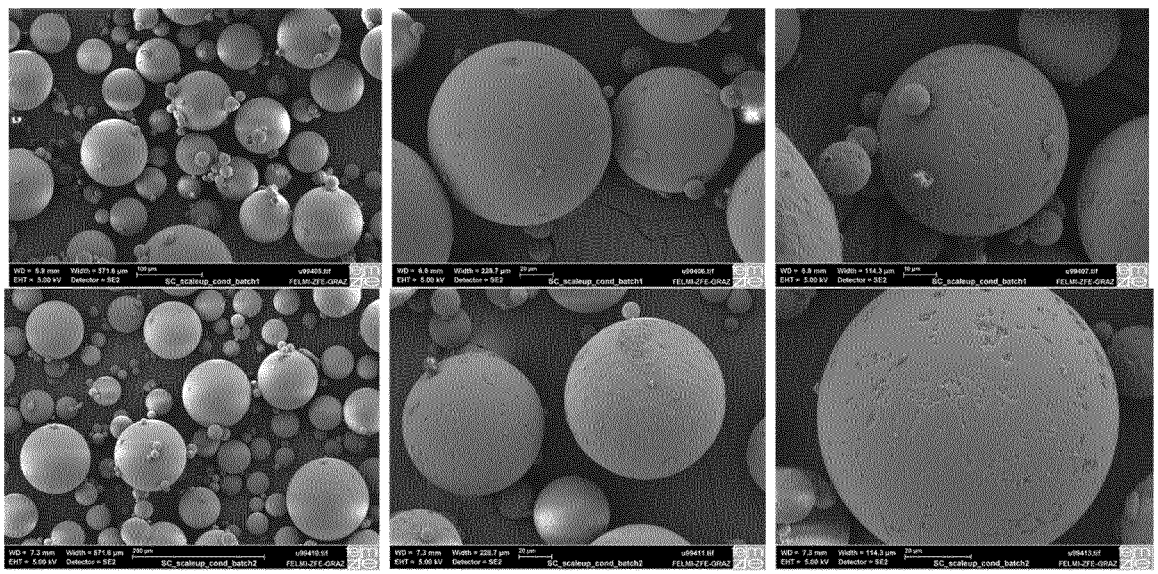

The morphology of the particles was examined using a scanning electron microscope (SEM) (Zeiss Ultra 55, Zeiss, Oberkochen, Germany) operating at 5 kV. The samples were mounted on a carbon tape and gold-palladium sputtered prior to analysis (FIG. 2).

The shape factor analysis was performed as follows. A sample of the spray congealed powder was isolated by means of a graduated spatula (19 mm³ of sample), the aliquot was loaded into the Morphology G3 sample holder (optical microscopy image analysis system, Malvern Morphology G3 Ver. 8.12) and dispersed on a dedicated glass slide with a controlled pressure (1 bar) using a dedicated dispersion chamber. The image analysis was performed using a 5× objective on a selected area (a circular area with a radius of 25 mm) to guarantee at least 20000 particles were measured. The measurement parameters were set to acquire individual particles for shape analysis and any sampling anomalies i.e. multiple particles were removed by a software filter.

The roundness factor (RN) was determined using the equation $RN=p^2/4\pi A$, where p is the perimeter and A is the area. Particle Shape factor (PSF) was calculated with the Morphology software using the equation 1/RN (this factor is called HS Circularity in the Malvern Morphology terminology). The powder exhibited a uniform spherical morphology as demonstrated by optical microscopy and SEM pictures (FIGS. 2 and 6). Particle shape factor (PSF) determined by image analysis of ~40000 individual particles gave an average value of 0.986 and confirmed the spherical morphology of the particles.

The physical state was investigated by WAXS at room temperature using a point focusing camera system S3-MICRO camera (Bruker AXS GmbH, Germany). The samples were filled into 2 mm diameter glass capillaries and analyzed under constant rotation (9 rpm/min) during 600 s at 30 counts/s.

WAXS results indicate that the found peak pattern of the conditioned sample corresponds to a mixture of α and β polymorph (δ mannitol gives rise to β mannitol), predominantly a (Burger at al., Journal of Pharmaceutical Science, 2000, Energy/temperature diagram and compression behavior of the polymorphs of D-mannitol).

Their micromeritics characterization was reported according to the following methods.

The particle size was determined by laser diffraction using an R1 lens (Sympatec HELOS). A sample of the powder was dispersed for two measurement conditions using an air pressure of 0.5 and 3 bar respectively (Sympatec RODOS) and sampled at a rate of 5 m/s from a controlled temperature and humidity dosing unit (Sympatec ASPIROS). The average d[v,10], d[v,50], d[v,90] values were calculated from triplicate measurements.

The span was calculated using the following equation:

$$\mathrm{Span}=[d(v,0.9)-d(v,0.1)]/d(v,0.5)$$

The specific surface area of the mannitol particles was investigated using the Micromeritics Tristar II 3020 (Norcross, USA). All samples were vacuum dried for two days at 25° C. using the Micromeritics VacPrep 061 degas unit (Norcross, USA). The measurements were performed using nitrogen adsorption and desorption isotherms at the temperature of liquid $N_2$ (−196° C.); Brunauer, Emmett, and Teller (BET) (Emmett, 1936) adsorption theory was used to calculate the specific surface area, using a pressure range of 0.05-0.30 normalized to the saturation pressure of the adsorbate.

1.5 g of powder was used, resulting in BET correlation factors above 0.999, indicating applicability of the method. Each measurement was carried out in triplicate.

The true density was determined by helium pycnometry (AccuPyc II 1340, Micromeritics, USA). The powder samples were accurately weighed and their volume measured in five consecutive runs, using 20 gas purges at 19.5 psi with and equilibrium rate of 0.005 psi/min. Particle density was calculated as the ratio of the sample mass and volume.

The characteristics of the three batches are reported in Table 1.

TABLE 1

|  | Batch 60 g scale | Batch 500 g n.1 | Batch 500 g n.2 |
| --- | --- | --- | --- |
| Specific Surface Area (m²/g) | 0.1621 | 0.1467 | 0.1173 |
| True density (g/cm³) | 1.4373 | 1.4533 | 1.4569 |
| PSD ($X_{10}$ – μm) | 31.07 | 32.0 | 31.2 |
| PSD ($X_{50}$ – μm) | 94.08 | 89.0 | 88.3 |
| PSD ($X_{90}$ – μm) | 208.20 | 189.6 | 184.1 |
| PSD (SPAN – μm) | 1.8 | 1.8 | 1.7 |

Example 2—Preparation of Formulations Comprising Carrier Particles According to the Invention The compound 1-(S)-1-[(3-cyclopropylmethoxy-4-difluoromethoxy)phenyl]-2-[(3,5-dichloro-1-oxy)-4-pyridinyl]

ethyl ester of 3-cyclopropylmethoxy-4-[(methanesulfonyl)-amino]-benzoic acid, hereinafter quoted as CHF 6001, was prepared according to the process disclosed in WO 2010/089107.

Mannitol particles were prepared as reported in Example 1.

CHF 6001 formulations (batch size 25 g) containing 4% w/w drug were prepared by mixing in a high-shear mixer (Hosokawa Lab Cyclomix, Japan) for 20 min at 100 rpm or 250 rpm.

The homogeneity of the prepared mixtures was checked at the end of the mixing procedure. For each formulation ten samples (of 20 to 60 mg each) were collected from different spots of the powder bed. Each sample was dissolved in 50 mL of an appropriate solvent ($CH_3CN$/water 60:40 v/v solution) and the quantification of the drug was performed by HPLC-UV.

Homogeneity was assumed at a coefficient of variation (calculated as the percentage of the ratio between standard deviation and mean value of the ten measurements) lower than 5%. Assay is expressed as % with respect to the theoretical content claim.

The results are reported in Table 2.

TABLE 2

| Batch | Mixing Time (min) | Mixing Speed (RPM) | Assay (%) | RSD (%) |
| --- | --- | --- | --- | --- |
| Batch 1 | 20 | 100 | 96.6 | 3.9 |
| Batch 2 | 20 | 250 | 97.0 | 1.5 |
| Batch 3 | 20 | 250 | 96.8 | 0.9 |

Example 3—In Vitro Aerodynamic Performances

The powder formulation of Example 3 was characterized in terms of aerosol performances after loading it in the multidose dry powder inhaler described in WO 2004/012801, and known as NEXThaler®. The average formulation shot weight is dependent on the density of the powder and for this formulation was around 20 mg. The nominal strength of the tested formulation (4% w/w drug loading) corresponded to 800 µg/20 mg a shot.

In vitro aerodynamic assessment was performed using a Next Generation Impactor (NGI, Copley Scientific, UK) equipped with a USP induction port a pre-separator, seven impaction stages and a final micro-orifice collector.

After completing the assembly, the NGI was connected to a vacuum pump and the flow rate through the impactor was measured by a mass flowmeter.

Critical Flow (P3/P2 ratio) was ≤0.5 at the sampling flow rate of 60 mL/min.

Once connected the device to the impactor through an airtight rubber mouth, the vacuum pump was activated at a flow of 60 L/min for 4 seconds so that 4 L of air were drawn through the apparatus according to Ph. Eur. 8.0, 2.9.18.

The drug CHF 6001 deposited on each stage of the impactor was recovered from NGI using the solvent $CH_3CN:H_2O$ (60:40% v/v) dispensed into the induction port (including mouthpiece—50 mL), pre-separator (100 mL), and each stage (10 mL). All samples were analyzed by HPLC-UV.

The aerodynamic particle size distribution was based on 2 actuations from the NEXThaler®, a multi-dose device described in WO 2004/012801, and in particular from page 1 first line to page 39, last line), each sampled into 4 liters of air (equivalent to an inhalation time of 4 s).

The aerodynamic performance was evaluated by calculating:

emitted dose (ED), obtained as the sum of the portions of drug recovered in all the parts of the impactor expressed in µg, and its percentage with respect to the nominal dose;

fine particle mass (FPM), namely the quantity of drug with a cut-off diameter lower than 5 µm, calculated by interpolation according to the European Pharmacopoeia (Ph. Eur. 8.0, 2.9.18) and expressed in µg;

the fine particle fraction (FPF), calculated as the ratio of the FPM to the ED expressed as percentage;

the mean mass aerodynamic diameter (MMAD), calculated as the median of the distribution of airborne particle mass with respect to the aerodynamic diameter.

The results of the aerosol performances are reported in Table 3.

TABLE 3

| Batch | Mixing Time (min) | Mixing Speed (rpm) | Theoretical dose µg | ED µg | ED % | FPM µg | FPF % | MMAD (µm) |
| --- | --- | --- | --- | --- | --- | --- | --- | --- |
| Batch 1 | 20 | 100 | 800 | 770.8 | 96.35 | 320.5 | 41.6 | 2.1 |
| Batch 2 | 20 | 250 | 800 | 768.1 | 96.01 | 322.2 | 41.9 | 2.0 |

As it can be appreciated, good aerosol performances were obtained with all the preparations, with FPF significantly higher than 40%.

Excellent values in terms of percentages of the emitted doses were obtained.

Similar results regarding the percentage of the emitted dose were obtained by replacing CHF 6001 with beclometasone dipropionate at the same nominal dose for shot (800 µg/20 mg).

The invention claimed is:

1. A pharmaceutical composition comprising one or more active ingredients in physical admixture with spray-congealed carrier particles consisting of mannitol, wherein:
    the pharmaceutical composition is in the form of a dry powder for inhalation;
    the pharmaceutical composition is formulated so that the one or more active ingredients are delivered in a single dose of 800 micrograms to 1 mg per actuation of an inhaler during use;
    the particles have a mass diameter of 30 to 300 micrometers;
    the particles a shape factor of 0.80 to 1.15; and
    the particles are obtained by a process comprising:

i) heating mannitol until completely melted;
ii) spraying the molten mannitol through a pressure nozzle into a spray congealing chamber to obtain droplets;
iii) cooling the droplets to induce solidification and particle formation;
iv) separating the obtained particles; and
v) conditioning the particles.

2. The pharmaceutical composition according to claim 1, wherein the particles have a shape factor of 0.90 to 1.10.

3. The pharmaceutical composition according to claim 1, wherein the particles have a shape factor of 0.95 to 1.05.

4. The pharmaceutical composition according to claim 1, wherein the particles have a mass diameter of 30 to 280 micrometers.

5. The spray pharmaceutical composition according to claim 1, wherein the particles have a mass diameter of 30 to 250 micrometers.

6. The pharmaceutical composition according to claim 1, having the particles have a specific surface area of 0.09 to 0.26 $m^2/g$.

7. The pharmaceutical composition according to claim 1, the particles have a true density of 1.3 to 1.6 $g/cm^3$.

8. The pharmaceutical composition according to claim 1, wherein conditioning comprises storing the particles at room temperature in a sealed chamber at 90-97% relative humidity for 12-48 hours.

9. A process for preparing the pharmaceutical composition according to claim 1, the process comprising mixing the spray congealed mannitol carrier particles with one or more active ingredients in a high-shear mixer.

10. A dry powder inhaler filled with the pharmaceutical composition according to claim 1.

11. A package comprising the pharmaceutical formulation according to claim 1, and a dry powder inhaler.

* * * * *